(12) United States Patent
Yu et al.

(10) Patent No.: US 8,524,245 B2
(45) Date of Patent: Sep. 3, 2013

(54) USE OF ANTRODIA CAMPHORATA FOR TREATING GOUT

(75) Inventors: Chieh-Chou Yu, Miaoli County (TW); Cheng-Chung Wei, Taichung (TW)

(73) Assignee: Chieh-Chou Yu, Miaoli County (TW)

( * ) Notice: Subject to any disclaimer, the term of this patent is extended or adjusted under 35 U.S.C. 154(b) by 0 days.

(21) Appl. No.: 13/434,850

(22) Filed: Mar. 30, 2012

(65) Prior Publication Data

US 2012/0183571 A1   Jul. 19, 2012

Related U.S. Application Data

(63) Continuation-in-part of application No. 12/689,960, filed on Jan. 19, 2010.

(51) Int. Cl.
*A61K 36/07*   (2006.01)

(52) U.S. Cl.
USPC .................................................... 424/195.15

(58) Field of Classification Search
None
See application file for complete search history.

(56) References Cited

U.S. PATENT DOCUMENTS 6,740,517 B2 * 5/2004 Lan et al. .................. 435/254.3

FOREIGN PATENT DOCUMENTS

CN        100371450        2/2008

OTHER PUBLICATIONS

Chian-Ju Yang, "Assessment of solid-state culture of *Antrodia cinnamomun mycelia* extracts on antitumor effect and mechanisms in cultured hepatoma cells," Jun. 2006, Taiwan (Full Foreign Document + English Translation of Abstract Provided).
Kuei-Rong Yen, "Effect of *Antrodia camphorata* on Plasma Glucose and Antioxidation in STZ-Induced Hyperglycemic Rats," Jul. 2002, Taiwan (Full Foreign Document + English Translation of Abstract Provided).
YC Hseu et al., "Antioxidant activity of *Antrodia carnphorata* on free radical-induced endothelial cell damage," J Ethnopharmacol. Jul. 23, 2008;118(2):237-45 (Only Abstract Provided).
U.S. Appl. No. 12/689,960, "Office Action" mailed Jun. 14, 2012 (11 pages).
U.S. Appl. No. 12/689,960, "Office Action Response", filed Apr. 15, 2012 (11 pages).
Horiba et al., "Neointimal formation in a restenosis model is suppressed in midkine-deficient mice", The Journal of Clinical Investigation, vol. 105. No. 4, Feb. 2000, 489-495.

* cited by examiner

*Primary Examiner* — Susan Hoffman
(74) *Attorney, Agent, or Firm* — Lowe Hauptman & Ham, LLP

(57) ABSTRACT

The present invention relates to the use of antrodia camphorata in the treatment of skin conditions, such as acne vulgaris, urticaria and eczema, allergic rhinitis, diabetes mellitus and its complications, cancer cachexia, hypercholesterolemia, gout in a subject in need of such treatment. The present invention is also directed to the use of antrodia camphorata in the prevention and treatment of oral cancer and arterial restenosis, in a subject in need of such prevention. The methods comprise the steps of: identifying a subject in need thereof, and administering to the subject a formulation comprising an effective amount of antrodia camphorata, whereby the symptoms in the subject are reduced or prevented. The composition can be a pharmaceutical composition or a nutraceutical composition.

8 Claims, 3 Drawing Sheets

USE OF ANTRODIA CAMPHORATA FOR TREATING GOUT

This application is a continuation-in-part application of U.S. patent application Ser. No. 12/689,960, filed on 19 Jan. 2010, which is incorporated by reference in its entirety.

FIELD OF THE INVENTION

The present invention relates to methods of treating skin conditions, allergic rhinitis, diabetes mellitus and its complications, cancer cachexia, hypercholesterolemia, and the prevention of oral cancer and restenosis in an artery by a composition comprising antrodia camphorata.

BACKGROUND OF THE INVENTION

Antrodia camphorata, also known as "niu-chang chih", is a native fungus in Taiwan. Its spores grow on the inner cavity of the decayed cinnamomum Kanehirai Hey, at an altitude between 450 to 2,000 meters. The fruiting body has a bell-shape, plate-shape, or horseshoe shape appearance and the color varies from orange to brown. The phytochemical investigations showed that antrodia camphorata comprises of polysaccharides (30-50%), triterpenoids (30%), steroids, superoxide dismatase and amino acids.

Antrodia camphorata was first noticed by the indigenous people in Taiwan as a perfect remedy for alcoholic hangover and alcohol-related liver disease. The fruiting bodies of antrodia camphorata are believed to be effective against inflammation, liver diseases, and gastrointestinal upset in Taiwanese fold medicine.

Acne Vulgaris

Acne vulgaris is a common skin disease characterized by noninflammatory comedones and by inflammatory papules, pustules, and nodules. Twenty percent of the patients with acne vulgaris have severe acne, resulting in permanent physical and mental scarring. It mainly affects face, the upper part of the chest, and the back, where there are most sebaceous follicles. Acne vulgaris may be due to blocked and infected skin pores secondary to a build up of excess skin oil, bacteria and other tissue. The standard therapies for acne vulgaris include topical or oral antibiotics, oral contraceptive and sporonolactone but current treatments are associated with variable side effects (Strauss J S et al, J Am Acad Dermatol; 56(4):651-63, 2007).

Urticaria

Urticaria, commonly referred to as hives, affects 15-20% of the general population at some time during their lifetime. It appears as raised, well-circumscribed areas of erythema and edema involving the dermis and epidermis that are very itchy. Pruritus (itching) and rash are the primary manifestations of urticaria. Urticaria results from the release of histamine, bradykinin, leukotriene C4, prostaglandin D2, and other vasoactive substances from mast cells and basophils in the dermis. These substances cause extravasation of fluid into the dermis, leading to the urticarial lesion. The intense pruritus of urticaria is a result of histamine released into the dermis. Acute urticaria is usually self-limited and commonly resolves within 24 hours but may last longer. Chronic urticaria, on the other hand, lasts more than 6 weeks. Neither acute nor chronic urticaria results in long-term consequences other than anxiety and depression. Current therapies to treat urticaria include antihistamine and corticosteroid but they are variably effective against chronic urticaria (Zuberbier T et al. Allergy 61(3): 321-31, 2006).

Eczema

Eczema, also known as atopic dermatitis, is an allergic condition that affects the skin. The exact cause of eczema is not known, although it is activated by the immune system and is related to allergic reactions. Eczema can be triggered by just about anything coming in contact with the skin. Common triggers of eczema include soaps, detergents, weather (hot, cold, humid, or dry), environmental allergens, gloves, even emotional or mental stress. It occurs in atopic people, who are extra sensitive to skin irritation. Eczema causes intense itching and burning, and the skin appears dry, flaky and red. Repeated scratching of the rash can cause skin sores and cracks, which are susceptible to bacteria, even viral infection. These infections are usually very minor, but they do require treatment with antibiotics or they may become very severe.

Eczema is a very common condition, and it affects all races and ages, including young infants. About 1-2 percent of adults have eczema, and as many as 20 percent of children are affected. It usually begins early in life, as most affected individuals have their first episode before the age of five. Eczema may fade in adulthood, but people who have eczema tend to have lifelong skin irritation and related problems.

Chronic eczema can be a difficult, frustrating condition. Prescription-strength steroid cream and antihistamine medication are the usual treatments. For severe cases not responding to high-potency steroid cream, alternate treatments may be tried. These include coal tar, psoralen plus ultraviolet A light, and immunosuppresive agents. However, most of the eczema treatments are slow and not always effective.

Allergic Rhinitis

Allergic rhinitis, also known as hay fever, is characterized by inflammation of the nasal mucosal lining, usually caused by dust mites, animals, pollens, molds and food. The inflammation generates excessive amounts of mucus, causing nasal congestion, nasal discharge, sore throat, sneezing, and post-nasal drip. Allergic rhinitis may cause additional symptoms such as itching of the throat and/or eyes, excessive tearing, headache, facial pressure, and edema around the eyes. These symptoms may vary in intensity from the nuisance level to debilitating. (Kim et al. Current Opinions in Otolaryngology & Head and Neck Surgery 15: 268-273, 2007). Many groups of medications are used for allergic rhinitis, including antihistamines, corticosteroids, decongestants, saline, sodium cromolyn, antileukotrienes and immunotherapy (Compalati E et al. Ann Allergy Asthma Immunol 102(1):22-8, 2009)

Cancer Cachexia

Cachexia may be defined as reduced carcass weight. Cancer cachexia is a complex syndrome with anorexia, weight loss, wasting of muscle and adipose tissues, hyperlipidemia, and other metabolic abnormalities, usually seen at an advanced stage of cancer. The causes of cancer-related cachexia are multi-fold, such as anorexia and early satiety. Early satiety can be due to direct encroachment of a tumor on the gastrointestinal tract, atrophic changes in the mucosa and muscles of the stomach, and a reduction in the duration or activity of digestive enzymes may lead to delayed gastric emptying and slowing of peristalsis (Kufe D et al, Cancer Medicine 7th Ed, 2006)

The patients affected appear chronically ill and emaciated, there is significant loss of body fat, muscle, and other components. The definitive treatment of cancer cachexia is removal of the causative tumor. Short of achieving this goal, various measures, such as steroid, megestrol acetate, and enteral or parenteral nutrition, have been undertaken with varying degrees of success.

Diabetes Mellitus

Diabetes mellitus (DM) is a group of disorders characterized by hyperglycemia and is associated with microvascular (ie, retinal, renal), macrovascular (ie, coronary, peripheral vascular), and neuropathic (ie, autonomic, peripheral nerve) complications. Hyperglycemia results from lack of endogenous insulin, which is either absolute, as in type 1 DM, or relative, as in type 2 DM.

The diagnosis of DM is readily entertained when a patient presents with classic symptoms (ie, excessive urination, excessive thirst, increased appetite, and weight loss). More commonly, the diagnosis is made when the health care provider discovers either the fasting plasma glucose is greater than or equal to 126 mg/dL on 2 occasions or the random glucose is greater than or equal to 200 mg/dL (Report of the expert committee on the diagnosis and classification of diabetes mellitus. Diabetes Care 26 Suppl 1:S5-20, 2003). Conventional treatments for DM include oral hypoglycemia agent and insulin injections, and hypoglycemia is the most important complication for both forms of treatment.

Hypercholesterolemia

The guidelines of the American Heart Association and the NCEP Adult Treatment Panel III (ATP III) define hypercholesterolemia as a blood cholesterol concentration of greater than or equal to 240 mg/dL (desirable cholesterol concentrations are less than 200 mg/dL). The condition is caused by a number of factors, including atherogenic diet (excessive intake of saturated fat, trans fat, and, to a lesser extent, cholesterol), obesity, and sedentary lifestyle.

Hypercholesterolemia is usually discovered during routine screening and does not produce symptoms. Hypercholesterolemia is more common in individuals with a family history of the condition, but lifestyle factors (e.g., a diet high in saturated fat) clearly play a major role. The primary manifestation of hypercholesterolemia is coronary artery disease. (Lewington S. et al, Lancet. Dec. 1, 2007; 370(9602):1829-39.

Medical therapy for hypercholesterolemia involves lifestyle and diet modification and pharmacologic therapy, such as HMG-CoA reductase inhibitors (statins). However, statin is associated with side effects including inflammation of the liver, muscle inflammation, pain, and weakness.

Gout

Gout is a common disorder of uric acid metabolism that can lead to deposition of monosodium urate (MSU) crystals in soft tissue, causing recurrent episodes of debilitating joint inflammation. Acute episodes of gout often lead to incapacitation. Typically, the smaller, lower-extremity joints are involved. Podagra (inflammation of the first metatarsophalangeal joint) is the initial joint manifestation in 50% of cases. Untreated chronic gout can lead to severe joint destruction and renal damage, due to MSU deposition in the kidney.

Acute flares of gout can result from situations that lead to increased levels of serum uric acid, such as the consumption of beer or liquor, overconsumption of foods with high purine content, trauma, hemorrhage, dehydration, or underexcretion of uric acid include renal insufficiency, chronic alcohol abuse.

Options for treatment of acute gout include pain relief and colchicines, a classic treatment that is now rarely indicated due to its risk of toxicity. Allopurinal is commonly used for chronic gout but it is associated with many risks, such as develop dyspepsia, headache, diarrhea, and/or pruritic maculopapular rash. Less frequently, patients taking allopurinol can develop allopurinol hypersensitivity, which carries a mortality rate of 20-30%.

Oral Cancer

Oral cancer is particularly common in the developing world. The etiology appears to be multifactorial and is strongly related to lifestyle, mostly habits and diet (particularly tobacco, betel, or alcohol use), although other factors, such as infective agents (e.g. human papillomaviruses), are also implicated (Scully C et al. Oral Oncol. 38(3):227-34, 2002).

The oral cavity is 1 of the 10 most frequent sites of cancer internationally with three quarters of cases affecting people in the developing world, where, overall, oral cancer is the third most common cancer after stomach and cervical cancer. An estimated 378,500 new cases of oral cancer are diagnosed annually worldwide. In certain countries, such as Sri Lanka, India, Pakistan, and Bangladesh, oral cancer is the most common cancer. A recent study in Taiwan (an endemic betel quid chewing area) found between 1979 and 2003, the oral cancer incidence rates increased 6.19 times in males and 2.32 times (Che-Wei Hsu at http://ir.cmu.edu.tw/ir/handle/310903500/608).

The conventional treatments for oral cancer include surgery, radiation and chemotherapy. Despite these treatment modalities, the five-year survival rate for oral cancer is only around 60% according to American Cancer Society.

Arterial Restenosis

For patients with coronary artery blockage, angioplasty is a safe and effective way to unblock coronary arteries. During this procedure, a catheter is inserted into the groin or arm of the patient and guided forward through the aorta and into the coronary arteries of the heart. There, blocked arteries can be opened with a balloon positioned at the tip of the catheter or with the placement of small metallic spring-like devices called "stents." The implanted stent serves as a scaffold that keeps the artery open. Restenosis is the result of neointima formation and can occur after angioplasty or the use of steins. (Horiba M et al. J. Clin. Invest. 105(4): 489-495, 2000) It usually occurs within 6 months after the initial procedure and the chance of restenosis is 25%.

Restenosis may produce symptoms that are very similar to the symptoms of coronary artery blockage, such as chest pain triggered by exertion. If restenosis is a possibility, the cardiologist may refer the patient for an exercise ECG test or a repeat cardiac catheterization. Drugs and vitamins administered either orally or intravenously have been tested for prevention of restenosis, but have not been consistently shown to be helpful. (Dangas G et al Circulation. 105:2586-2587, 2002) It would therefore be desirable to have a method to prevent the restenosis occurrence.

Despite the advance in medicine over the last 50 years, there is still a need for effective, economic and safe methods for treating skin conditions such as acne vulgaris, urticaria, and eczema, allergic rhinitis, cancer cachexia, diabetes mellitus and hypercholesterolemia. There is also a need for effective, economic and safe methods for preventing oral cancer and restenosis.

SUMMARY OF THE INVENTION

The present invention is directed to a method of preventing restenosis in an artery. The method comprising the step of identifying a subject in need thereof, and administering to the subject a composition comprising an effective amount of antrodia camphorata, whereby the disease in the subject are prevented.

The present invention is directed to a method of treating skin condition. The method comprising the step of identifying a subject in need thereof, and administering to the subject a composition comprising an effective amount of antrodia camphorata whereby the symptoms of the disease in the subject are reduced.

The present invention is directed to a method of treating allergic rhinitis. The method comprising the step of identifying a subject in need thereof, and administering to the subject a composition comprising an effective amount of antrodia camphorata whereby the symptoms of the disease in the subject are reduced.

The present invention is directed to a method of treating diabetes mellitus and its complications. The method comprising the step of identifying a subject in need thereof, and administering to the subject a composition comprising an effective amount of antrodia camphorata, whereby the symptoms of the disease in the subject are reduced.

The present invention is directed to a method of treating cancer cachexia. The method comprising the step of identifying a subject in need thereof, and administering to the subject a composition comprising an effective amount of antrodia camphorata, whereby the symptoms of the disease in the subject are reduced.

The present invention is directed to a method of treating hypercholesterolemia. The method comprising the step of identifying a subject in need thereof, and administering to the subject a composition comprising an effective amount of antrodia camphorata, whereby the symptoms of the disease in the subject are reduced.

The present invention is directed to a method of preventing oral cancer. The method comprising the step of identifying a subject in need thereof, and administering to the subject a composition comprising an effective amount of antrodia camphorata, whereby the disease in the subject are prevented.

DETAILED DESCRIPTION OF THE INVENTION

Figure 1:
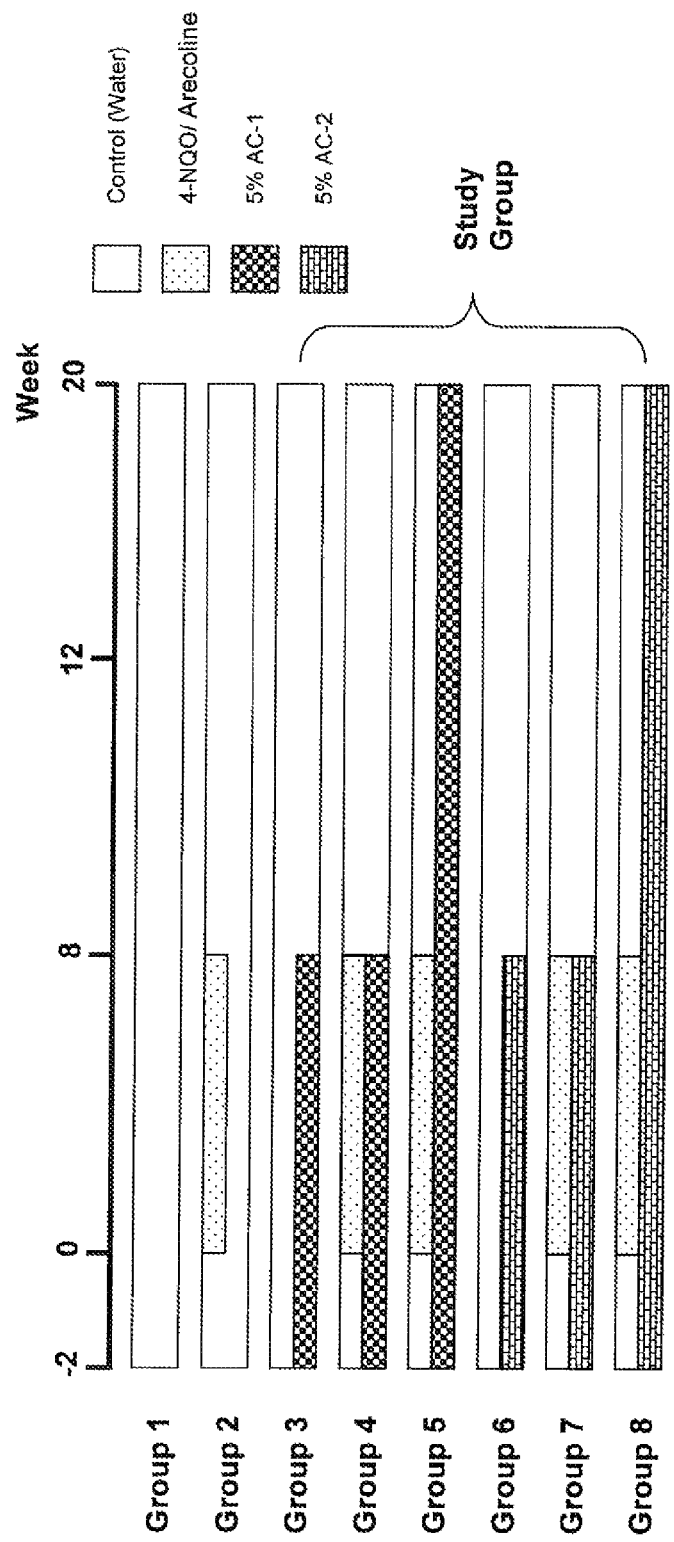
FIG. 1 shows the study design of antrodia camphorata in preventing oral cancer in mice.

The inventor discovered that antrodia camphorata is useful for treating a skin conditions, allergic rhinitis, diabetes mellitus, cancer cachexia, hypercholesterolemia, and preventing the development of oral cancer and restenosis in an artery.

Antrodia Camphorata

Antrodia camphorata is a native fungus in Taiwan. It is commercially available and can be prepared by known methods, for example, U.S. Pat. No. 6,395,271, which is incorporated herein by reference. The fruiting bodies of antrodia camphorata are harvested from cinnamomum Kanehirai Hey, baked in an oven at 50° C. for days and grounded to powder. Antrodia camphorata powder are placed into capsules for patient consumption.

Antrodia camphorata can be used as is, or it can be administered in the form of a pharmaceutical composition that additionally contains a pharmaceutically acceptable carrier. In addition, antrodia camphorata may be given in the form of a nutraceutical composition to treat and prevent diseases.

A "pharmaceutically acceptable carrier" refers to a carrier that, after administration to or upon a subject, does not cause undesirable physiological effects. The carrier in a pharmaceutical composition must be "acceptable" also in the sense that is compatible with the antrodia camphorata and, preferably, capable of stabilizing it. One or more solubilizing agents can be utilized as pharmaceutical carriers for delivery of antrodia camphorata. Suitable pharmaceutically acceptable carriers are well known in the art and vary with the desired form and mode of administration of the pharmaceutical composition. For example, they may include, but not limited to, biocompatible vehicles, adjuvants, additives (such as pH-adjusting additives), diluents, preservatives, or excipients such as fillers, binders, wetting agents, disintegrators, surface-active agents, lubricants and the like.

The above pharmaceutical composition can be prepared by any method known in the art of pharmacy. Such methods include the step of brining into association the active compound with the carrier which may encompass one or more accessory ingredients. For instance, for oral administration in the formal of a tablet or capsule, antrodia camphorata can be comminuted with an oral, non-toxic pharmaceutically acceptable inert carrier such as ethanol, glycerol, water and the like. Powders are prepared by comminuting antrodia camphorata to a suitable fine size and mixing with a similarly comminuted pharmaceutical carriers such as an edible carbohydrate, for example, starch or mannitol. Flavoring, dispersing and coloring agents can also be present. In another instance, antrodia camphorata can be incorporated into any acceptable carrier, including creams, gels, lotions or other types of suspensions that can stabilize the active ingredient and deliver it to the affected area by topical applications.

The term "nutraceutical" as used herein denotes a usefulness in the nutritional application. Thus, the nutraceutical compositions can find use as supplement to food and beverages. The term nutraceutical composition also comprises food and beverages containing antrodia camphorata.

The composition can be applied by any of the accepted modes of administration including inhalation, topical, oral, and parenteral (such as intravenous, intramuscular, subcutaneous or rectal). Oral administration is preferred.

Skin Condition

The inventor of the present invention has discovered that antrodia camphorata is effective in treating skin conditions. The method comprises the steps of identifying a subject suffering from the skin condition, and administering to the subject a composition comprising an effective amount of antrodia camphorata, whereby the symptoms of the skin conditions are reduced. An "effective amount," as used herein, refers to a dose of antrodia camphorata that is sufficient to eradicate or reduce the symptoms and signs of the skin conditions, such as inflammatory pastules, itching, and rash.

In one embodiment, the skin rash is acne vulgaris. In another embodiment, the skin rash is urticaria. In another embodiment, the skin rash is eczema.

Allergic Rhinitis

The inventor of the present invention has discovered that antrodia camphorata is effective in treating allergic rhinitis. The method comprises the steps of identifying a subject suffering from allergic rhinitis, and administering to the subject a composition comprising an effective amount of antrodia camphorata, whereby the symptoms of allergic rhinitis are reduced. An "effective amount," as used herein, refers to a dose of antrodia camphorata that is sufficient to eradicate or reduce the symptoms and signs of allergic rhinitis, such as nasal congestion, nasal discharge, post-nasal drip, sore throat, sneezing, headache, itching of the nose and throat, facial pressure and pain, and general malaise.

Diabetes Mellitus

The inventor of the present invention has discovered that antrodia camphorata is effective in treating diabetes mellitus. The method comprises the steps of identifying a subject suffering from diabetes mellitus, and administering to the subject a composition comprising an effective amount of antrodia camphorata, whereby the symptoms of diabetes mellitus are reduced. An "effective amount," as used herein, refers to a dose of antrodia camphorata that is sufficient to eradicate or reduce the symptoms and signs of diabetes mellitus, such as excessive urination (polyuria), excessive thirst (polydipsia), excessive hunger and large intake of food (polyphagia), weight loss, and elevated blood sugar level.

Cancer Cachexia

The inventor of the present invention has discovered that antrodia camphorata is effective in treating cancer cachexia. The method comprises the steps of identifying a subject suffering from cancer cachexia, and administering to the subject a composition comprising an effective amount of antrodia camphorata, whereby the symptoms of cancer cachexia are reduced. An "effective amount," as used herein, refers to a dose of antrodia camphorata that is sufficient to eradicate or reduce the symptoms and signs of cancer cachexia, such as anorexia, weight loss, wasting of muscle and adipose tissues.

Hypercholesterolemia

The inventor of the present invention has discovered that antrodia camphorata is effective in treating hypercholesterolemia. The method comprises the steps of identifying a subject suffering from hypercholesterolemia, and administering to the subject a composition comprising an effective amount of antrodia camphorata, whereby the symptoms of hypercholesterolemia are reduced. An "effective amount," as used herein, refers to a dose of antrodia camphorata that is sufficient to eradicate or reduce the symptoms and signs of hypercholesterolemia, such as elevated serum cholesterol level.

Gout

The inventor of the present invention has discovered that antrodia camphorata is effective in treating gout. The method comprises the steps of identifying a subject suffering from gout, and administering to the subject a composition comprising an effective amount of antrodia camphorata, whereby the symptoms of gout are reduced. An "effective amount," as used herein, refers to a dose of antrodia camphorata that is sufficient to eradicate or reduce the symptoms and signs of gout, such as painful and inflamed joint.

Oral Cancer

The inventor of the present invention has discovered that antrodia camphorata is effective in preventing or treating oral cancer. The method comprises the steps of identifying a subject in need of oral cancer prevention, and administering to the subject a composition comprising an effective amount of antrodia camphorata, whereby the symptoms and signs of oral cancer are avoided or reduced. An "effective amount," as used herein, refers to a dose of antrodia camphorata that is sufficient to prevent or reduced the symptoms and signs of oral cancer, such as oral ulcer or oral mass.

Arterial Restenosis

The inventor of the present invention has discovered that antrodia camphorata is effective in preventing or treating restenosis in an artery. The method comprises the steps of identifying a subject in need of arterial restenosis prevention, and administering to the subject a composition comprising an effective amount of antrodia camphorata, whereby the symptoms and signs of arterial restenosis are avoided or reduced. An "effective amount," as used herein, refers to a dose of antrodia camphorata that is sufficient to prevent or reduced the symptoms and signs of arterial restenosis, such as chest pain, chest tightness, or abnormal angiography findings.

Methods of Administration

As a general proposition, about 1 g to about 8 g of antrodia camphorata per day will be an effective dosage for the pharmaceutical composition and the nutraceutical composition. The preferred dosage is about 4 g of antrodia camphorata per day. For lowering serum uric acid and the treatment of gout, the effective dosage is about 3.5 g to about 5.0 g of antrodia camphorata per day. In a preferred embodiment, the dosage is about 4.8 g of antrodia camphorata per day. In another preferred embodiment, the dosage is about 3.6 g of antrodia camphorata per day. The treatment interval may be from about once per day to four times per day. The dosage and treatment interval may vary somewhat depend upon several factors, including, but not limited to, the age and weight of the patient, route of administration, type of disease, how advanced the disease state is, any co-morbidity, or the co-administration of other medication.

Generally, subjects in need thereof take about 2 to about 10 capsules containing antrodia camphorata daily for treatment. Each capsule contains about 100 to about 800 mg of dry weight of antrodia camphorata, preferably about 300 to about 600 mg of dry weight of antrodia camphorata, and more preferably about 500 mg of dry weight of antrodia camphorata.

The term "about" as used herein covers the ranges claimed±15%.

Any method of delivering antrodia camphorata, including inhalation, topical, oral, and parenteral (such as intravenous, intramuscular, subcutaneous or rectal) is suitable for the present invention. Oral administration is preferred.

For skin condition, allergic rhinitis, and cachexia, the response to antrodia camphorata treatment is established by the disappearance of rash or acne, an improvement in running nose or nasal congestion, and an improvement of appetite and body weight, respectively. For diabetes mellitus, the response to antrodia camphorata is established by the measurement of serum glucose level or glycosylated proteins, such as Hemoglobin A1c. For hypercholesterolemia, the response to antrodia camphorata is established by the measurement of serum cholesterol level. For gout, the response to antrodia camphorata is established by the measurement of serum uric level and the resolution of painful and inflamed joint. The preventative or the treatment effect of antrodia camphorata on oral cancer is established by the avoidance of tumor development in the oral cavity. The effectiveness of antrodia camphorata in preventing restenosis in an artery can be determined by exercise ECG or angiography.

The following examples further illustrate the present invention. These examples are intended merely to be illustrative of the present invention and are not to be construed as being limiting.

EXAMPLE 1

Treatment of Acne Vulgaris

A female subject, aged 26, with severe acne vulgaris on her face for 2-3 years despite various medical treatments. She was treated with two antrodia camphorata tablets orally (400 mg of dry weight antrodia camphorata per tablet), three times a day, for two months. The acne on her face resolved and there was no new break out noted.

EXAMPLE 2

Treatment of Urticaria

A male subject, aged 47, with chronic urticaria (more than 6 months) had tried various treatment for 6 months without any improvement. He took two antrodia camphorata tablets (400 mg of dry weight antrodia camphorata per tablet), twice a day and the urticaria resolved after two months of treatment.

EXAMPLE 3

Treatment of Eczema

A male subject, aged 29, has chronic eczema since childhood. About 60-70% of his total body surface area was affected. He had recurrent eczema flare-ups and did not respond to topical steroid cream, and antihistamine. He also tried other treatments, including high dose intralesional steroid injection and immunosuppressive therapy with limited success. He took two antrodia camphorata tablets (400 mg of dry weight antrodia camphorata per tablet), twice a day orally and had immediately relief. There is no further eczema flare-up.

EXAMPLE 4

Treatment of Allergic Rhinitis

Antrodia camphorata was used to treat subjects who with allergic rhinitis. The results are summarized in Table 1.

EXAMPLE 5

Treatment of Cancer Cachexia

A male subject, aged 58, with metastatic thyroid cancer in palliative care, developed severe cancer cachexia. He took 3 g of antrodia camphorata twice a day. His appetite and energy level improved within 24 hours of taking antrodia camphorata and there was no further weight loss noted. Two months later, he ran out of antrodia camphorata and his condition deteriorated within 3 days after the discontinuation of antrodia camphorata. He became lethargic and could not take any food or fluid. He even required IV rehydration for 12 hours. He was recommenced on antrodia camphorata and his appetite improved within 24 hours of taking antrodia camphorata.

EXAMPLE 6

Treatment of Diabetes Mellitus

Subjects with diabetes mellitus were treated with antrodia camphorata. The results are summarized in Table 2.

TABLE 2

| Subject | Age and Sex | Pre-treatment blood glucose level | Dosage and route (400 mg of dry weight of antrodia camphorata per tablet) | Results AC glucose = ante cibum glucose PC glucose = post cibum glucose |
| --- | --- | --- | --- | --- |
| Subject 1 | 53 years old male | 563 mg/dl | 3 tablets three times a day | AC glucose 120 mg/dl, PC glucose 180 mg/dl |
| Subject 2 | 61 years old male | AC glucose 450 mg/dl | 5 tablets four times a day for 2 months | AC glucose 170 mg/dl, PC glucose 250 mg/dl |
| Subject 3 | 68 years old female | AC glucose 300 mg/dl | 2 tablets four times a day | AC glucose 140-150 mg/dl |
| Subject 4 | 54 years old female | 200 mg/dl | 3 tablets three times a day | After 2 months of treatment, serum glucose level reduced to 120 mg/dl |
| Subject 5 | 31 years old male | 483 mg/dl | 4 tablets three times a day | After one month of treatment, serum glucose level reduced to 117 mg/dl |
| Subject 6 | 73 years old male | 300 mg/d | 6 tablets per day | Serum glucose level reduced to 140 mg/dl. |

TABLE 1

| Subject | Dosage (400 mg of dry weight of antrodia camphorata per tablet) | Route of Administration | Duration | Results |
| --- | --- | --- | --- | --- |
| Subject 1 37 years old male | 2 tablets three times a day | Oral | 1 month | Symptoms relieved within 1 month |
| Subject 2 60 years old male | 1. ½ tablet twice a day 2. 4 tablets twice a day | 1. Inhalation 2. Oral | 3 months | Immediate relief of symptoms. |

EXAMPLE 7

Treatment of Hypercholesterolemia

Subjects with hypercholesterolemia were treated with antrodia camphorata. The results are summarized in Table 3.

TABLE 3

| Subject | Pre-treatment blood cholesterol level | Dosage and route (400 mg of dry weight antrodia camphorata per tablet) | Results |
| --- | --- | --- | --- |
| Subject 1, 52 years old male | 310 mg/dl | 3 tablets four times a day for 3 weeks | Blood cholesterol level reduced to 249 mg/dl after 3 weeks of treatment |

TABLE 3-continued

| Subject | Pre-treatment blood cholesterol level | Dosage and route (400 mg of dry weight *antrodia camphorata* per tablet) | Results |
|---|---|---|---|
| Subject 2, male | 305 mg/dl | 4 tablets twice a day for 2 months | Blood cholesterol level reduced to 158 mg/dl after 2 months of treatment |

EXAMPLE 8

Gout

A male subject, aged 46, was diagnosed with elevated serum uric acid level (11.2 mg/dl) He took six antrodia camphorata tablets (400 mg of dry weight antrodia camphorata per tablet), twice a day for 3 months. He did not take any additional medication to lower his serum uric level. His serum uric acid level was reduced to 8.9 mg/dl after 3 months of antrodia camphorata treatment.

EXAMPLE 9

Oral Cancer Trial

An in vivo evaluation of the preventative effect of antrodia camphorata in oral cancer was performed using C57BL/6JNarl mice population. Mice had free access to drinking water and food at all time during this trial.

AC-1: Antrodia camphorata cultivated from logs of Cinnamomum Kanehirai Hayata.

AC-2: Antrodia camphorata cultivated from shredded powder of Cinnamomum Kanehirai Hayata.

4-NQO stands for 4-nitroquinolin 1-oxide, it is a carcinogen which cause tumor in laboratory animals.

Arecoline (Are) is cytotoxic to cultured oral mucosal fibroblasts.

The investigators used 4-NQO and arecoline to induce oral cancer in mice

FIG. 1 showed the study design involving 8 study groups.

Group 1: ten mice were untreated for control analysis of baseline histology.

Group 2: ten mice were given 8 weeks 4-NQO/Are (Week 0 to Week 8).

Group 3: ten mice were given 10 weeks of 5% of AC-1 (Week-2 to Week 8).

Group 4: ten mice were given 8 weeks of 4-NQO/Are (Week 0 to Week 8) and 10 weeks of AC-1 (Week-2 to Week 8).

Group 5: ten mice were given 8 weeks of 4-NQO/Are (Week 0 to Week 8) and 22 weeks of AC-1 (Week-2 to Week 20).

Group 6: ten mice given 10 weeks of 5% AC-2 (Week-2 to Week 8).

Group 7: ten mice were given 8 weeks of 4-NQO/Are (Week 0 to Week 8) and 10 weeks of AC-2 (Week-2 to Week 8).

Group 8: ten mice were given 8 weeks of 4-NQO/Are (Week 0 to Week 8) and 22 weeks of AC-2 (Week-2 to Week 20).

During the 20-week trial period, the mice were examined on regular intervals (Week 0, Week 8, Week 12, Week 16, and Week 20) for the manifestation of oral cancer such as:

A red lesion

An ulcer with fissuring or raised exophytic margins

A white or mixed white and red lesion

An indurated lump/ulcer (i.e., a firm infiltration beneath the mucosa)

A lesion fixed to deeper tissues or to overlying skin or mucosa

The results of the study are summarized in Table 4. 50% of the Group2 mice (ingested 8 weeks of 4-NQO/Are but no antrodia camphorata) developed oral cancer at the end of Week 20, whereas 30% of Group 4 mice (ingested 8 weeks of 4-NQO/Are and 10 week of AC-1) and 10% of Group 5 mice (ingested 8 weeks of 4-NQO/Are and 22 week of AC-1) developed oral cancer.

Similarly, 20% of Group 7 mice (ingested 8 weeks of 4-NQO/Are and 10 week of AC-2) and 40% of Group 8 mice (ingested 8 weeks of 4-NQO/Are and 22 week of AC-2) developed oral cancer. The results show AC-1 may be effective in preventing oral cancer; however, the data had no statistical significance.

TABLE 4

Tumor incidence (%) in mice taking 4-NQO, AC-1 and AC-2

| | W 0 | W 8 | W 12 | W 16 | W 20 |
|---|---|---|---|---|---|
| Group 1 (Control) | 0 | 0 | 0 | 0 | 0 |
| Group 2 (4-NQO/Are) | 0 | 0 | 10 | 30 | 50 |
| Group 3 (AC-1) | 0 | 0 | 0 | 0 | 0 |
| Group 4 (4-NQO/Are+ 10 weeks of AC-1) | 0 | 0 | 10 | 20 | 30 |
| Group 5 (4-NQO/Are+ 22 weeks of AC-1) | 0 | 0 | 10 | 10 | 10 |
| Group 6 (AC-2) | 0 | 0 | 0 | 0 | 0 |
| Group 7 (4-NQO/Are+ 10 weeks of AC-2) | 0 | 0 | 0 | 10 | 20 |
| Group 8 (4-NQO/Are+ 22 weeks of AC-2) | 0 | 0 | 10 | 30 | 40 |

EXAMPLE 10

Restenosis Trial

Figure 2:
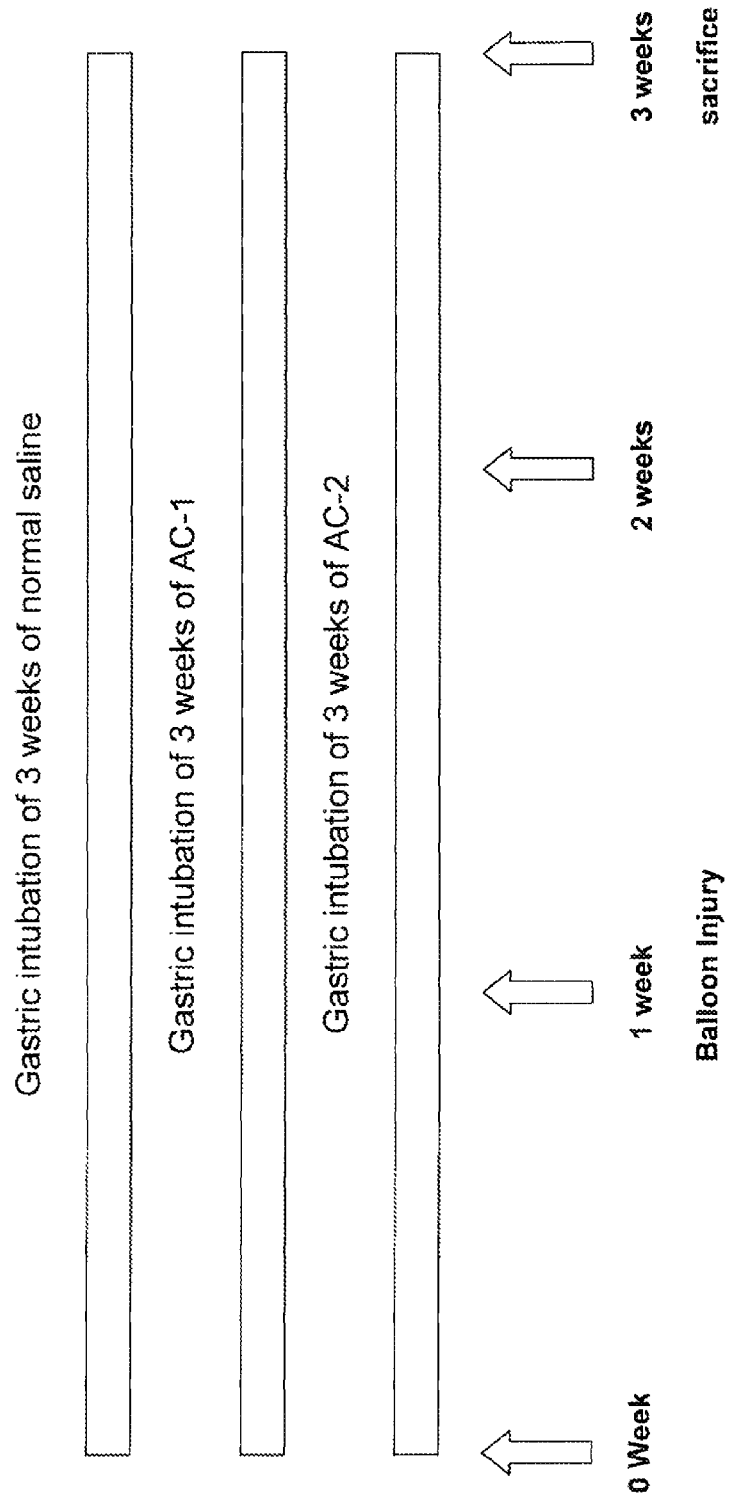
FIG. 2 shows the study design of antrodia camphorata in preventing arterial restenosis in mice.

An in vivo evaluation of the preventative effect of antrodia camphorata in arterial restenosis was performed in mice. FIG. 2 shows the study design involving 3 study groups.

Group C: mice fed with normal saline via gastric intubation for 3 weeks (Week 0 to Week 3).

Group 1C: mice fed with AC-1 via gastric intubation for 3 weeks (Week 0 to Week 3). (Note: AC-1 is antrodia camphorata cultivated from logs of Cinnamomum Kanehirai Hayata).

Group 2C: mice fed with AC-2 via gastric intubation for 3 weeks (Week 0 to Week 3). (Note: AC-2 is antrodia camphorata cultivated from shredded powder of Cinnamomum Kanehirai Hayata.)

Balloon injury to the arterial wall was induced in all mice in Week 1. Balloon injury can cause restenosis in the artery as a result of neointimal formation.

Figure 3:
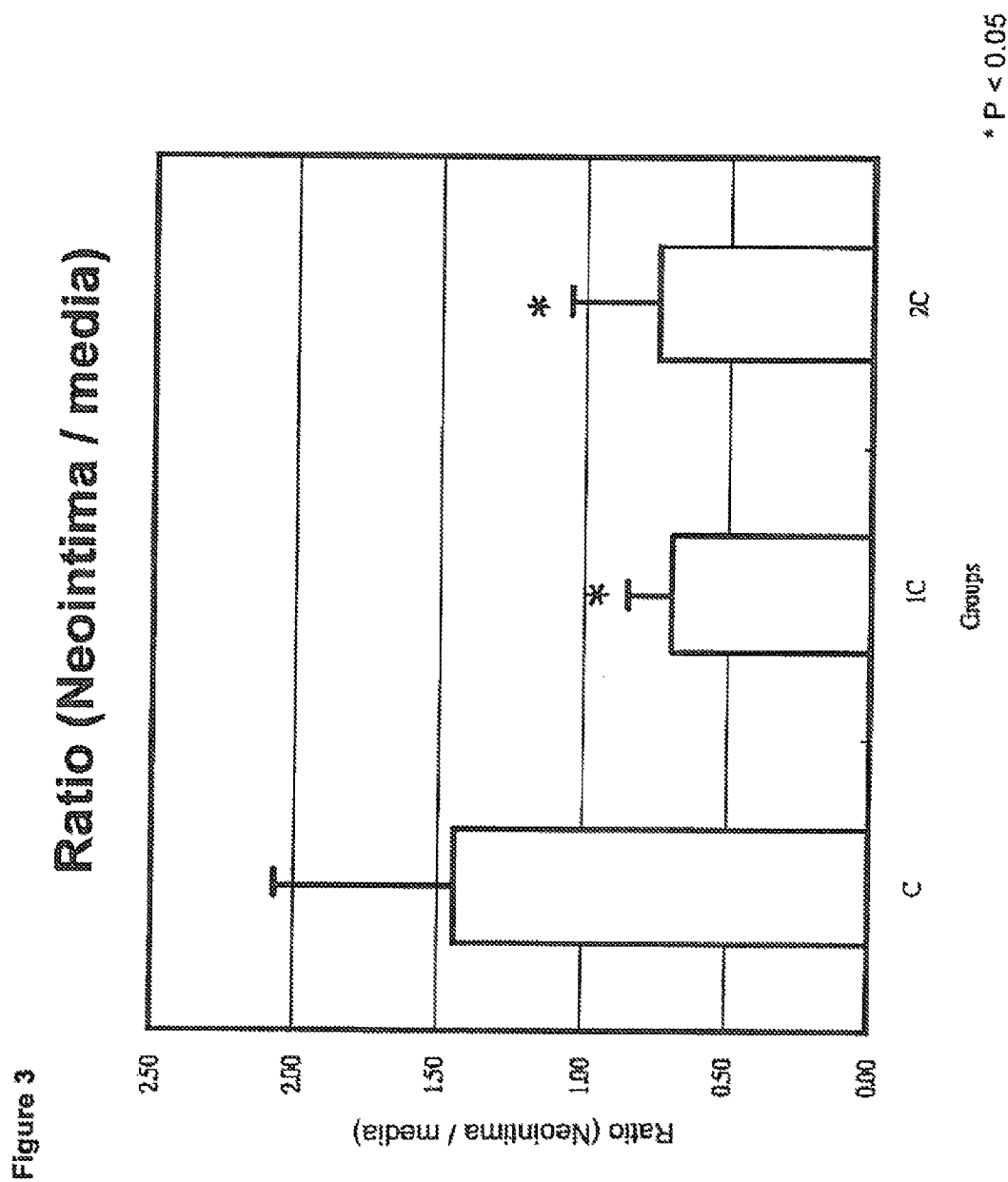
FIG. 3 shows the neointima/media ratios in mice treated with normal saline (C), antrodia camphorata cultivated from logs of Cinnamomum Kanehirai Hayata (1C) and antrodia camphorata cultivated from shredded powder of Cinnamomum Kanehirai (2C). The use of antrodia camphorata in mice significantly reduces the neointima/media ratio.

At the end of 3 week trial period, all mice were sacrificed and their arteries were examined using H&E stain. The results are summarized in FIG. 3. The neointima/media ratios in the antrodia camphorata groups (AC-1 and AC-2) are significantly less than the control group (c). The results show that antrodia camphorata is effective in preventing neointimal formation and restenosis in an artery.

EXAMPLE 11

Serum Uric Acid Trial

A twelve-week, randomized, double-blind study was performed in 36 patients to evaluate the effect of antrodia camphorata in serum uric acid.

The patient was included in the study if he or she has all of the following:

Patients over the age of 20;
Serum ALT level is between 55.5 to 740 IU/I;
Serum total bilirubin level is ≦2 mg/dl; and
Prothrombin time is ≦3 seconds.

The patient was excluded in the study if he or she has any of the following:

Past history of hepatoma;
Receiving anti-viral or interferone therapy;
Women who are pregnant or lactating;
Receiving chemotherapy;
Hepatitis B;
Alcohol abuse during the trial period; or
ICU admission within 3 months of the trial.

Patients were randomized into placebo (n=8) and treatment (n=16) groups. Patients in the treatment group took 1.8 g of antrodia camphorata, twice a day, for 12 weeks. Table 5 shows the baseline demographic characteristics of the treatment and placebo groups.

TABLE 5

| | Treatment (n = 24) | Placebo (n = 11) | p value |
|---|---|---|---|
| Age (years) [b] | 39.5 (13.5) | 49.0 (24.0) | 0.241 |
| Gender (male %) | 18 (75.0%) | 9 (81.8%) | 1.000 |
| Weight (kg) [b] | 72.00 (13.25) | 74.00 (21.00) | 0.778 |
| Height(cm) [b] | 168.0 (13.0) | 164.0 (15.0) | 0.832 |
| BMI [b] | 27.31 (3.37) | 26.14 (3.09) | 0.538 |
| Systolic blood pressure (mmHg) [b] | 130.5 (16.0) | 134.0 (20.0) | 0.832 |
| Diastolic blood pressure (mmHg) [b] | 82.5 (16.0) | 84.0 (12.0) | 0.958 |
| Mean blood pressure (mmHg) [b] | 98.00 (13.67) | 101.00 (13.00) | 0.944 |
| WBC($mm^3$) [b, c] | 6.81 (2.97) | 7.51 (2.70) | 0.610 |
| RBC(mm) [b] | 513.5 (58.0) | 500.0 (82.0) | 0.197 |
| Hb (gm/dL) [b] | 14.95 (1.95) | 16.00 (2.50) | 0.711 |
| Ht(%) [b] | 45.10 (5.35) | 45.60 (7.00) | 0.597 |
| MCV(fl) [a] | 85.68 ± 7.76 | 90.49 ± 1.88 | 0.008 |
| MCH(g/dL) [a] | 29.04 ± 3.16 | 30.66 ± 1.36 | 0.041 |
| MCHC(g/dL) [b] | 33.8 (1.70) | 34.2 (1.30) | 0.916 |
| Platelet($mm^3$) [a, c] | 252.5 (93.0) | 250.0 (55.0) | 0.846 |
| GPT (IU/l) [a] | 90.33 ± 42.10 | 77.36 ± 26.56 | 0.356 |
| GOT (IU/l) [a] | 52.54 ± 37.78 | 38.09 ± 13.46 | 0.107 |
| Albumin (g/dl) [a] | 6.73 ± 10.71 | 4.49 ± 0.34 | 0.316 |

TABLE 5-continued

| | Treatment (n = 24) | Placebo (n = 11) | p value |
|---|---|---|---|
| Total Cholesterol (mg/dl) [b] | 184.5 (41.5) | 170.0 (71.0) | 0.222 |
| Triglycerides (mg/dl) [a] | 175.79 ± 142.45 | 103.36 ± 48.79 | 0.034 |
| uric acid (mg/dl) [a] | 6.66 ± 1.64 | 6.23 ± 1.62 | 0.474 |
| Blood glucose (mg/dl) [a] | 102.0 ± 14.37 | 105.82 ± 17.82 | 0.503 |
| Creatinine (mg/dl) [a] | 0.79 ± 0.23 | 0.73 ± 0.21 | 0.439 |
| γ-GT (IU/l) [a] | 110.79 ± 195.50 | 40.00 ± 21.87 | 0.093 |
| Alk-P (IU/l) [a] | 78.88 ± 41.39 | 52.82 ± 19.20 | 0.016 |
| Total Bilirubin (mg/dl) [a] | 0.79 ± 0.35 | 0.66 ± 0.20 | 0.263 |
| Bilirubin direct (mg/dl) [a] | 0.18 ± 0.17 | 0.09 ± 0.06 | 0.032 |
| prothrombin time prolongation (sec) | 10.43 ± 0.43 | 10.58 ± 0.15 | 0.138 |
| PTA [a, d] | 4.58 ± 1.79 | 5.18 ± 1.29 | 0.328 |
| PGA [a, e] | 4.61 ± 1.36 | 5.07 ± 1.30 | 0.352 |
| SF-36 [a, f] | 577.59 ± 143.47 | 511.06 ± 112.85 | 0.185 |
| vitality [b] | 60.0 (20.00) | 55.0 (20.00) | 0.658 |
| physical functioning [a] | 87.29 ± 16.28 | 83.18 ± 13.83 | 0.474 |
| bodily pain [a] | 70.79 ± 20.59 | 74.55 ± 19.41 | 0.614 |
| general health perceptions [b] | 56.0 (31.0) | 57.0 (17.0) | 0.972 |
| physical role functioning [a] | 75.00 ± 39.01 | 38.64 ± 37.69 | 0.014 |
| emotional role functioning [a] | 77.78 ± 33.57 | 60.61 ± 41.68 | 0.202 |
| social role functioning [a] | 83.85 ± 16.27 | 75.00 ± 12.50 | 0.120 |
| mental health [a] | 70.0 (32.0) | 68.0 (16.0) | 0.608 |

[a] mean ± SD,
[b] median (IQR)

During the 12-week trial period, the patient's serum uric acid level was checked at baseline, 4, 8 and 12 weeks after the commencement of the treatment. At the end of 12-week trial period, the serum uric acid was reduced by 053 mg/dl in the treatment group and reduced by 0.09 mg/dl in the placebo group. The results show that antrodia camphorata is effective in lowering serum uric acid level.

What is claimed is:

1. A method for treating gout, comprising the steps of:
   identifying a subject suffering from gout; and
   administering to the subject 2.4 g to about 5 g of dry weight of antrodia camphorata per day, whereby the symptoms and signs of gout in the subject are reduced.

2. The method according to claim 1, wherein about 4.8 g of dry weight of antrodia camphorata is administered per day.

3. The method according to claim 1, wherein about 3.6 g of dry weight of antrodia camphorata is administered per day.

4. The method according to claim 1, wherein said antrodia camphorata is formulated as a pharmaceutical composition.

5. The method according to claim 1, wherein said antrodia camphorata is formulated as a nutraceutical composition.

6. The method according to claim 1, wherein the said administering is oral administration.

7. The method according to claim 1, wherein said subject is a human.

8. The method according to claim 1, wherein said subject is an animal.

* * * * *